US00PP36135P2

(12) United States Plant Patent
McMahon et al.

(10) Patent No.: US PP36,135 P2
(45) Date of Patent: Sep. 24, 2024

(54) ***POPULUS* PLANT NAMED 'NextGen'**

(50) Latin Name: ***Populus* x *euramericana***
Varietal Denomination: NextGen

(71) Applicant: REGENTS OF THE UNIVERSITY OF MINNESOTA, Minneapolis, MN (US)

(72) Inventors: Bernard G. McMahon, Coon Rapids, MN (US); William Berguson, Duluth, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/517,841

(22) Filed: Nov. 22, 2023

Related U.S. Application Data

(60) Provisional application No. 63/431,226, filed on Dec. 8, 2022.

(51) Int. Cl.
*A01H 5/00* (2018.01)
*A01H 6/00* (2018.01)

(52) U.S. Cl.
USPC ..... Plt./218

(58) Field of Classification Search
USPC ..... Plt./218
See application file for complete search history.

*Primary Examiner* — Susan McCormick Ewoldt
(74) *Attorney, Agent, or Firm* — Penny J. Aguirre

(57) ABSTRACT

The invention is a new and distinct variety of male *Populus* tree named 'NextGen' that is characterized by its superior to above average field growth performance, its excellent to above average rooting rate, its disease resistance to foliar rusts (*Melampsora* sp.), leaf spots (*Marssonina* sp.) and stem cankers (*Septoria* sp.), its vigorous vegetative growth and production in nursery stoolbeds, its cold hardiness for overwintering and surviving in Minnesota with no frost damage, its wide-spread superior growth performance in many test locations (ie: MN, MI, WI, IA, IN, NY, etc); able to be considered "geo-robust" after years of testing, its replicated growth testing and evidence of promising performance and evaluation in phytoremediation research testing and applications, and its male flowers that do not produce seeds.

4 Drawing Sheets

STATEMENT REGARDING FEDERALLY SPONSORED RESEARCH

This invention was made with government support under 2018-68005-27635 awarded by the National Institute of Food and Agriculture, and DE-FC36-05GO85041 awarded by the U.S. Department of Energy. The government has certain rights in the invention.

Botanical classification: *Populus* x *euramericana*.
Variety denomination: 'NextGen'.

BACKGROUND OF THE INVENTION

The present invention relates to a new and distinct cultivar of *Populus* tree botanically known as *Populus* x *euramericana* (*Populus deltoides* x *Populus nigra*) 'NextGen', referred to hereafter by its cultivar name, 'NextGen'. *Populus* x *canadensis* is a hybrid between *Populus deltoides* and *Populus nigra*.

'NextGen' resulted from an ongoing research program at a research Institute in Duluth, Minnesota. The goal of the breeding program is to develop new cultivars of poplar trees with a fast growth habit, high disease resistance, hardiness, and geo-robust (adaptability to a wide range of growing sites) that are suitable for wood and biomass production.

'NextGen' originated from a cross made in March of 1999 between *Populus deltoides* 'D123' (not patented) as the female parent and *Populus nigra* 'N 949-2' (not patented) as the male parent. 'NextGen' was selected as a single unique plant from the seedlings that derived from the above cross in 2002.

Asexual propagation of the new cultivar was first accomplished by hardwood stem cuttings in February of 2002 under direction of the Inventors at a research nursery near Belle River, Minnesota. Asexual propagation of the new cultivar by hardwood stem cuttings has determined that the characteristics are stable and true to type in successive generations.

SUMMARY OF THE INVENTION

The following traits have been repeatedly observed and represent the characteristics of the new cultivar. These attributes in combination distinguish 'NextGen' as a new and unique cultivar of *Populus*.

1. 'NextGen' exhibits to above average field growth performance.
2. 'NextGen' exhibits to above average rooting rate.
3. 'NextGen' exhibits disease resistance to foliar rusts (*Melampsora* sp.), leaf spots (*Marssonina* sp.) and stem cankers (*Septoria* sp.).
4. 'NextGen' exhibits vigorous vegetative growth and production in nursery stoolbeds.
5. 'NextGen' exhibits cold hardiness for overwintering and surviving in Minnesota with no frost damage.
6. 'NextGen' exhibits a wide-spread superior growth performance in many test locations (ie: MN, MI, WI, IA, IN, NY, etc); able to be considered "geo-robust" after years of testing.

7. 'NextGen' exhibits replicated growth testing and evidence of promising performance and evaluation in phytoremediation research testing and applications.
8. 'NextGen' exhibits male flowers and therefore does not produce seeds.

The female parent of 'NextGen' differs from 'NextGen' in being difficult to root and in having susceptibility to leaf-rust and a less vigorous growth habit. The male parent of 'NextGen' differs from 'NextGen' in having variable rooting ability. 'NextGen' can be compared to the *Populus* cultivars 'DN5' (not patented) and 'NM6' (not patented). 'DN5' and 'NM6' are both similar to 'NextGen' in being useful for establishment commercially. 'DN5' differs from 'NextGen' in having a much lower growth rate, lower rooting consistency, and lower establishment rate. 'NM6' differs from 'NextGen' in having less disease resistance and a lower survival rate and growth rate in MN, IN, MI, and NY.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosure on websites includes listings by The University of Minnesota.

BRIEF DESCRIPTION OF THE DRAWINGS

The accompanying color photographs illustrate the overall appearance and distinct characteristics of the new *Populus*.

The photographs in FIG. 1 and FIG. 2 were taken of 7-year-old plants of 'NextGen' as grown outdoors in a trial field in Cohasset, Minnesota.

Figure 1:
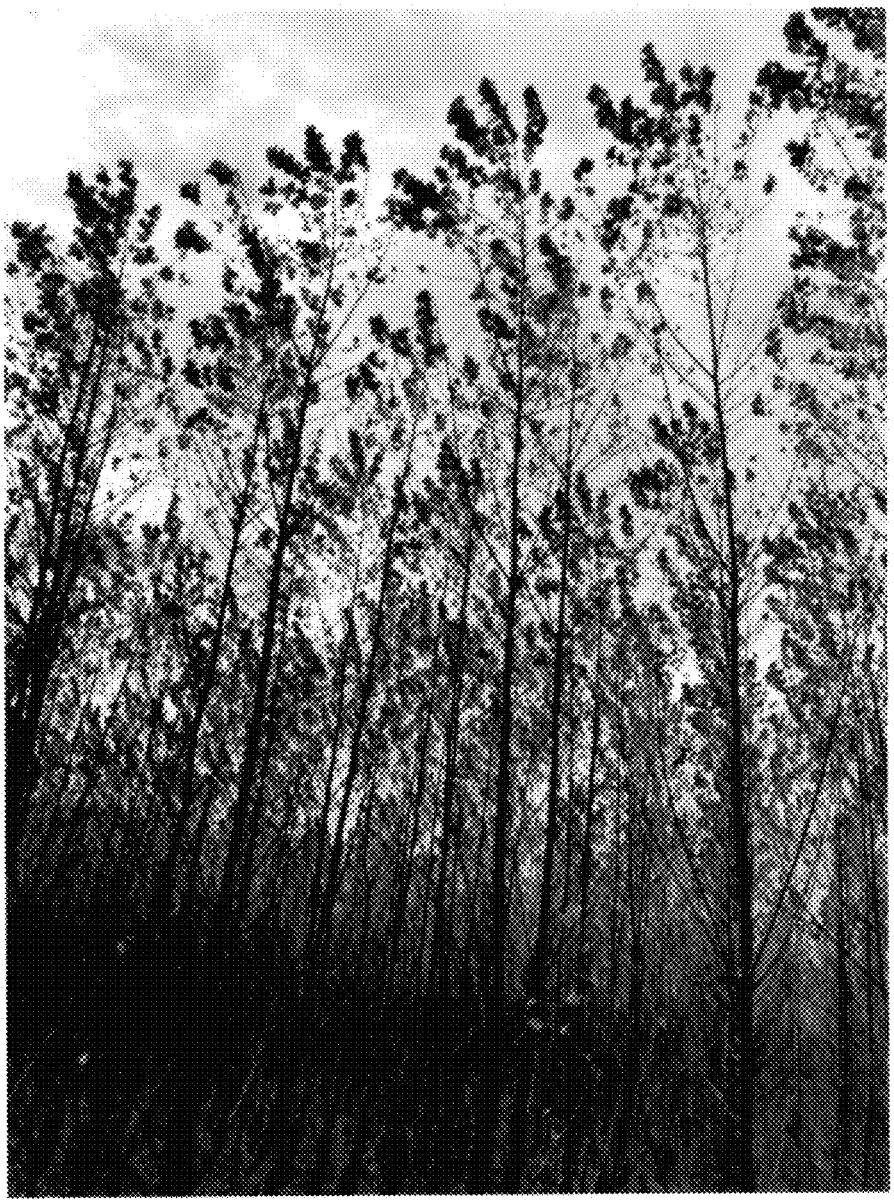

The photograph in FIG. 1 provides a view of a planting of multiple plants of 'NextGen'.

Figure 2:
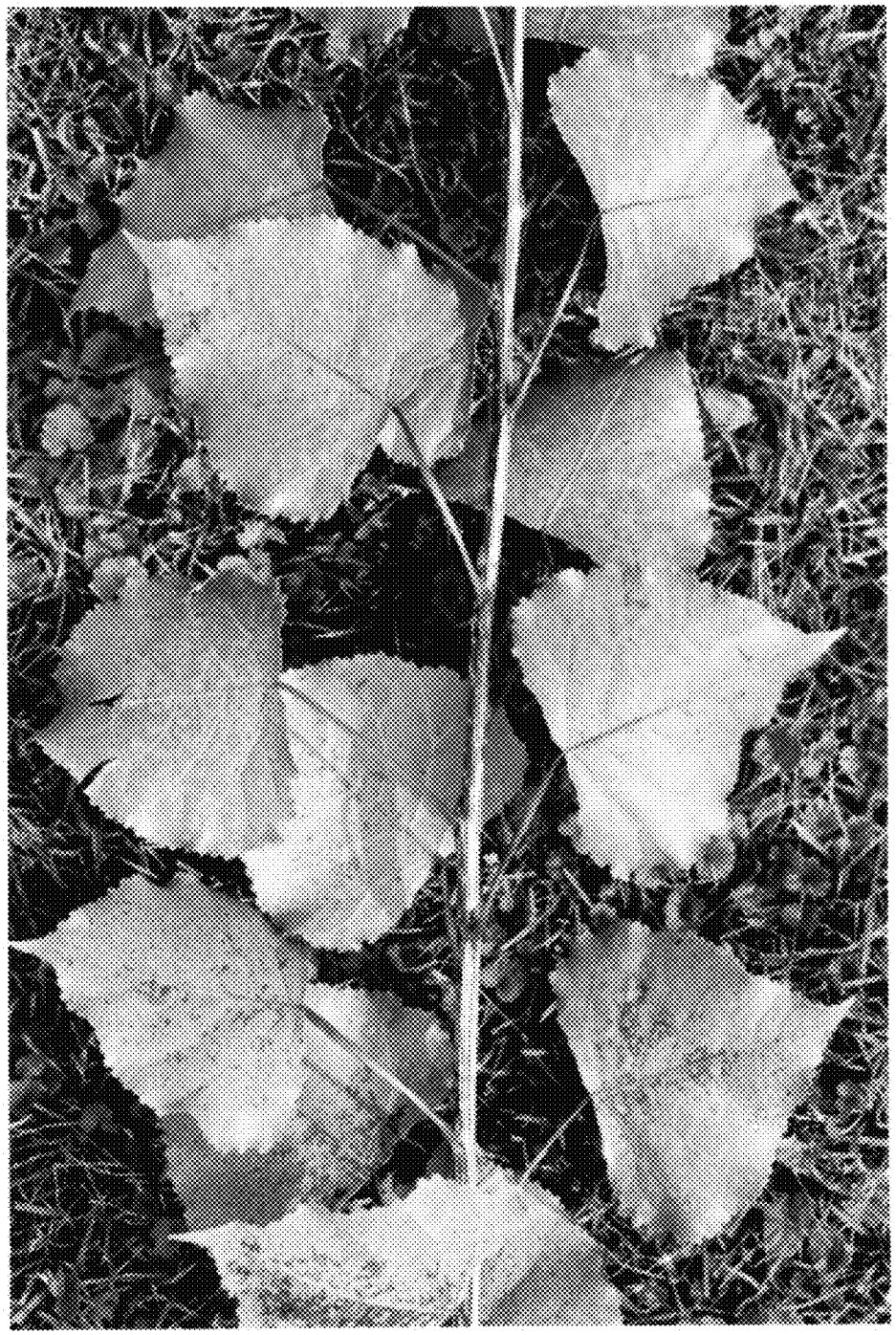

The photograph in FIG. 2 provides a close-up view of the fall foliage of 'NextGen'.

Figure 3:
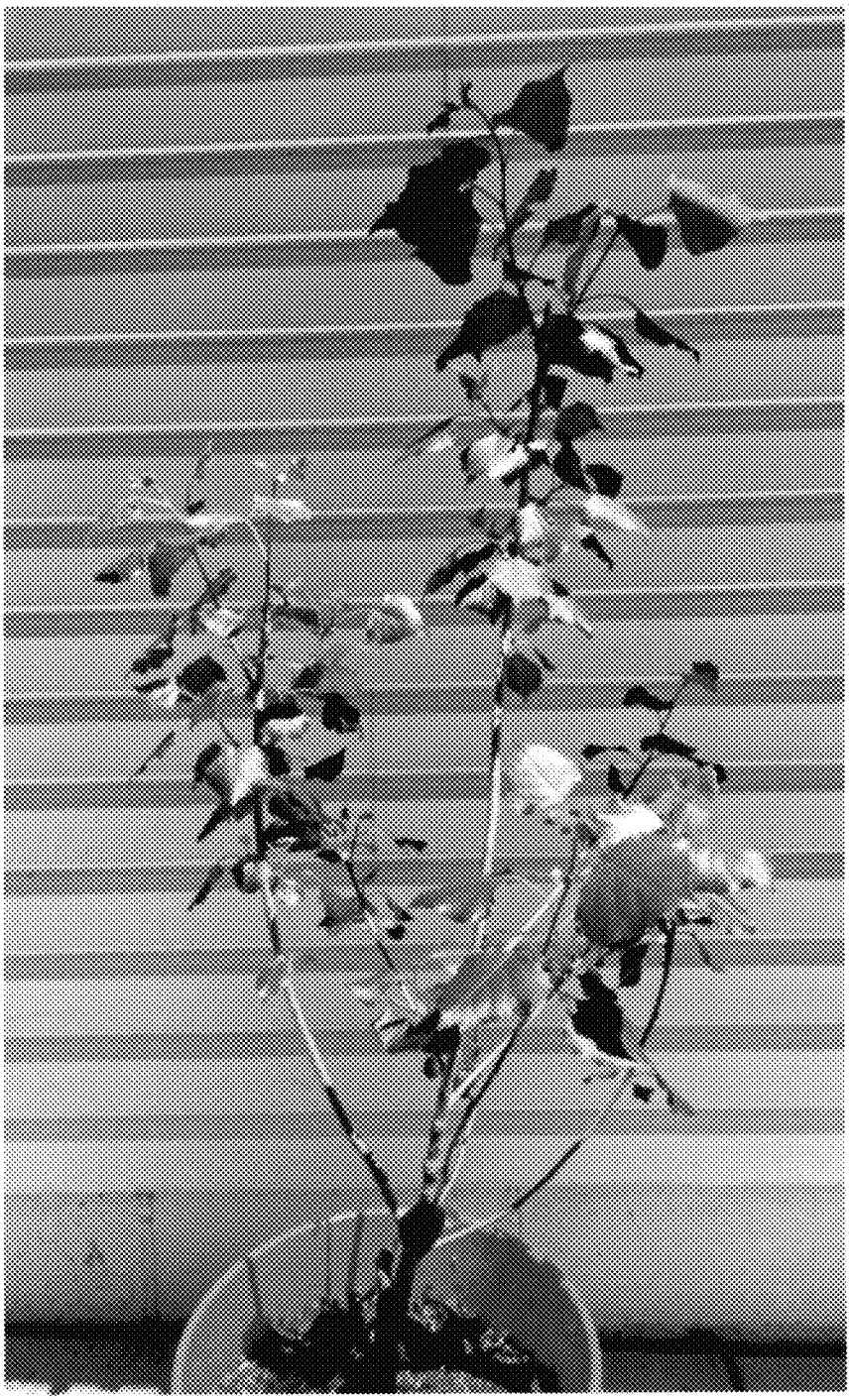
Figure 4:
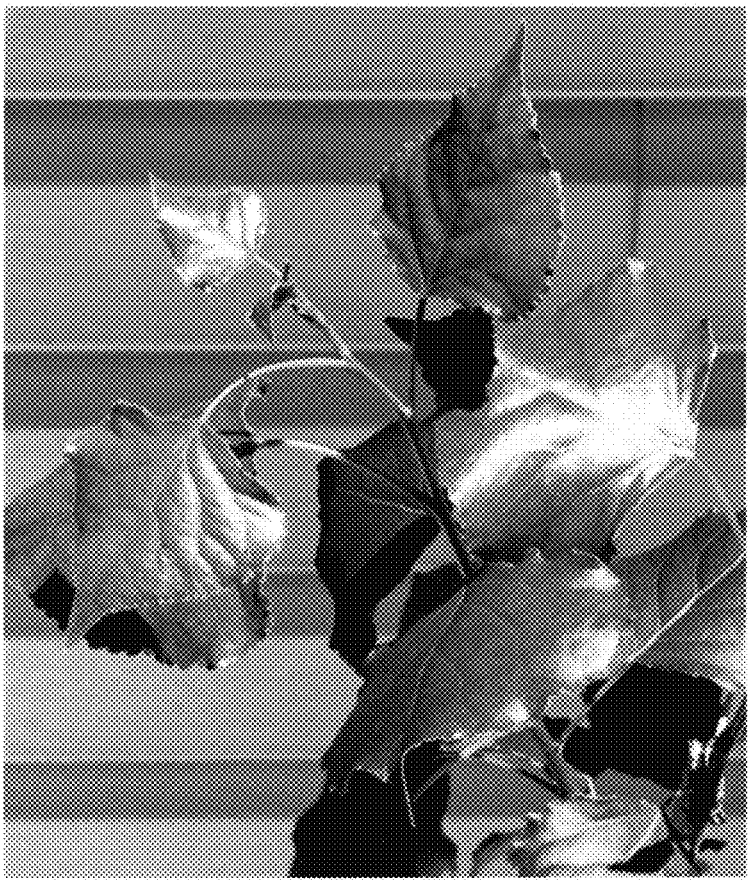

The photographs in FIG. 3 and FIG. 4 were taken of plants of 'NextGen' in their second season of growth, having grown in a nursery stoolbed in Cohasset, Minnesota, for 1 year then transferred to grow outdoors in 5-gallon containers in Duluth, Minnesota.

The photograph in FIG. 3 provides a side view of 'NextGen'.

The photograph in FIG. 4 provides a view of the young foliage of 'NextGen'.

Figure 5:
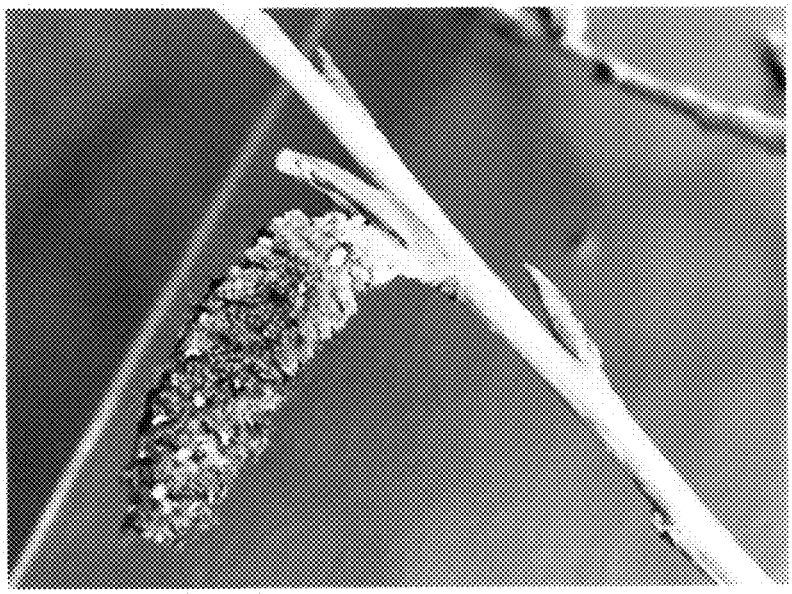

The photograph in FIG. 5 was taken from a branch forced into bloom from a 7-year-old plant of 'NextGen' that was growing in a trial bed in Cohasset, Minnesota and provides a view of a male catkin.

The colors in the photographs are as close as possible with the photographic and printing technology utilized and the values cited in the detailed botanical description accurately describe the colors of the new *Populus*.

DETAILED BOTANICAL DESCRIPTION

The following is a detailed description of plants of 'NextGen' in their second season of growth, having grown in a nursery stoolbed in Cohasset, Minnesota, for 1 year then transferred to grow outdoors in 5-gallon containers in Duluth, Minnesota. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming habit.*—Dioecious, bearing colorful male flowers (staminate catkins) in late April through May in Cohasset, MN, flowering commences on plants 5 to 7 years in age.

*Plant habit.*—Deciduous tree.

*Plant habit.*—Slightly spreading.

*Height and spread.*—An average of 112 cm height and 66 cm in spread as plants in their second season of growth, having grown in a nursery stoolbed for 1 year then transferred to grow outdoors in 5-gallon containers.

*Cold hardiness.*—At least to U.S.D.A. Zones 3.

*Root description.*—Fibrous, 199B in color.

*Diseases and pests.*—Has shown resistance to foliar rusts (*Melampsora* sp.), leaf spots (*Marssonina* sp.) and stem cankers (*Septoria* sp.), no resistance or susceptibility to pests has been observed.

*Growth rate.*—Vigorous.

*Propagation.*—Hardwood stem cuttings.

*Root development.*—Time required for root initiation is an average of 30 days, time required to produce a young tree from a rooted cutting is an average of 1 year, rooting rate >90%.

Branch description:

*Stem color.*—Young stems; 164A and 164B turning to 195A to 195B, flushed with 164A to 164B as it ages, mature stems; closest to 198A with slight undertones of 194A and 196D, trunk and old bark; a blend of N200B and 199B.

*Stem size.*—Main stems; average of 1.1 cm in diameter and 83 cm in length, lateral branches; average of 3 mm in diameter and 55 cm in length, trunk diameter; 2 cm.

*Stem surface.*—Young stems; glabrous, glossy, mature stems; dull with a slight sheen that makes the appearance glossy, rugose and moderately covered with lenticels; an average of 15 per 2 cm, round in shape, 2 mm in diameter, NN155C in color, trunk and old bark; rugose, matte.

*Branching.*—Densely branched; an average of 6 lateral branches per main branch, held upright at an average of 40° from the main branch.

*Internode length.*—Average of 11 cm.

Foliage description:

*Leaf shape.*—Triangular.

*Leaf division.*—Simple.

*Leaf base.*—Truncate.

*Leaf apex.*—Cuspidate.

*Leaf venation.*—Pinnate, color; young upper and lower surface N144A, mature upper and lower surface 142C.

*Leaf margin.*—Serrate and sinuate.

*Leaf attachment.*—Petiolate.

*Leaf arrangement.*—Alternate, whorled.

*Leaf surface.*—Young and mature leaves; both surfaces are glossy and glabrous.

*Leaf size.*—An average of 7 cm in length and 8 cm in width.

*Leaf internode length.*—An average of 1 cm.

*Leaf buds.*—1.5 cm in length, 3 mm in width, linear and pointed in shape, glossy and glabrous surface, color; 194A and 175A, an average 25 per lateral branch.

*Leaf color.*—Young upper and lower surface; 144A flushed with 175A, mature upper surface 147A, mature lower surface 147B, fall foliage colors; start of foliage changes a blend of N144A and 1A, at peak both surfaces a blend of 7A and 8A.

*Petioles.*—An average of 3.6 cm in length and 2 mm in width, flattened shape, 144A in color, surface glabrous and glossy.

Flower description (male flowers only):

*Catkin buds.*—Male; 3 cm in length, 1 cm in width, glossy and glabrous surface, a blend of 200B, 173A, and 173D.

*Bracts.*—Male; Alternate and overlapping until catkin burst, average of 3, very glossy and glabrous inner and outer surface, color; N199B and 203A, undertones of 154A, very sticky and waxy to the touch due to sap being produced, sap is high in quantity, 22A in color.

*Catkins.*—Pendulous and cylindrical in shape, staminate catkins appear in advance of the leaves, anthers and bracts whorling down the catkin stem, held in a drooping position from the scaly bud bract, male; first to burst, an average of 4 cm in length and 1.5 cm in diameter, color; en mass 59A, bract fringes 203A, base of bract fringe sometimes present en masse, NN155D, catkin stem 154C.

*Flowers.*—Male; average of 6 produced per lateral branch, anthers held in many disc-like sacs whorled in alternating groups of 3 around the center stem of the catkin, connected to the catkin stem with a short stem that is 2 mm in length, 1 mm in diameter, 154C in color, slightly glossy and glabrous surfaces, sac disk; oval in shape, 3 mm in width, 1.5 mm in length, 155A in color, matte in appearance, anthers; total average per catkin; 1,800, average of 30 per sac, 2 mm in length, 1 mm in width, oval in shape, basifixed, color: young anther color; outer edges and top flushed with 184B and 59A, centers 159A, old dehisces anthers; 8D, center 203A, filament; 1 mm in length, translucent with a sheen surface, NN155D in color, pollen; high in quantity, 11A in color, hairy bracts; protruding out in alternating positions down the catkin, fringed, silky-hairy bract scales, an average of 40 per catkin, bract size; average of 5 mm in length and width, individual hairs are less than 0.1 mm in size, coarse and matted appearance, densely hairy, 203A in color, center attachment; oval in shape, 2 mm in length, 1 mm in width, matte surfaces, 155A in color.

*Seed.*—None produced to date.

It is claimed:

1. A new and distinct variety of *Populus* tree named 'NextGen' as described and illustrated herein.

* * * * *